United States Patent [19]
Lauterbur et al.

[11] Patent Number: 6,088,611
[45] Date of Patent: *Jul. 11, 2000

[54] MODEL BASED METHOD FOR HIGH RESOLUTION DYNAMIC IMAGING

[75] Inventors: Paul C. Lauterbur; Zhi-Pei Liang; Hong Jiang, all of Urbana, Ill.

[73] Assignee: The Board of Trustees of the University of Illinois, Urbana, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/516,789

[22] Filed: Aug. 18, 1995

[51] Int. Cl.$^7$ .................................................. A61B 5/00
[52] U.S. Cl. ..................... 600/407; 600/410; 600/425; 600/509; 324/307; 378/4; 378/901
[58] Field of Search ............................. 128/653.2, 653.3, 128/696, 708; 324/307, 306, 309; 600/410, 419, 413, 509, 521, 407, 425; 378/4, 901

[56] References Cited

U.S. PATENT DOCUMENTS

| | | | |
|---|---|---|---|
| 4,663,591 | 5/1987 | Pelc et al. | 324/309 |
| 5,363,043 | 11/1994 | Xiang et al. | 324/309 |
| 5,363,044 | 11/1994 | Xiang et al. | 324/309 |
| 5,435,303 | 7/1995 | Bernstein et al. | 128/653.3 |
| 5,438,263 | 8/1995 | Dworkin et al. | 324/309 |

OTHER PUBLICATIONS

Ehman RL, Felmlee JP. Adaptive Technique for High–Definition MR Imaging of Moving Structures. Radiology 1989; 173:255–263.

Xiang QS, Henkelman RM. K–Space Description for MR Imaging of Dynamic Objects. Mag. Reson. Med. 1993; 29:422–438.

Lauzon ML, Rutt, BK. Generalized K–Space Analysis and Correction of Motion in MR Imaging. Magn. Reson. Med. 1993; 30:438–446.

Wood ML, Henkelman RM. Suppression of Respiratory Motion Artifacts in Magnetic Resonance Imaging. Med. Phys. 1986; 13:794–805.

Hedley M, Yan, H. Motion Artifact Suppression: A Review of Post Processing Techniques. Magn. Reson. Imaging 1992; 10:627–635.

Allebach JP. Analysis of Sampling–Pattern Dependance in Time–Sequential Sampling of Spatiotemporal Signals. J. Opt. Soc. Am 1981; 71:99–105.

Rahgozar MA, Allebach JP. A General Theory of Time–Sequential Sampling. Sig. Proc. 1992; 28:253–270.

*Primary Examiner*—Ruth S. Smith
*Attorney, Agent, or Firm*—Wildman, Harrold, Allen & Dixon; Gary R. Gillen

[57] ABSTRACT

Described here, is a method for obtaining high-resolution snap-shot images of moving objects in MR imaging applications through the elimination of ghosting and other image artifacts by estimating motion frequency data, estimating amplitude data for the motion frequency data, interpolating the motion frequency data and the amplitude data to generate snap-shot data frames, and generating snapshot images of each data frame.

12 Claims, 6 Drawing Sheets

6,088,611

MODEL BASED METHOD FOR HIGH RESOLUTION DYNAMIC IMAGING

BACKGROUND OF THE INVENTION

The invention herein described relates generally to magnetic resonance imaging (MRI). It finds particular applications in imaging "time-varying" objects such as the beating heart or abdomen. However, the invention is also applicable to other imaging modalities including X-ray CT (computerized tomography), PET (positron emission tomography), and the like.

In 1973 Dr. Paul C. Lauterbur introduced to the public the first MR generated image. Since then, great strides have been made in MR imaging techniques and machinery. In particular, MR imaging of selected parts of the human body is a favored and popular method used by doctors in medical diagnostic procedures. The advantages of MR imaging over other imaging modalities include high spatial resolution, non invasiveness, and the ease of both 2-dimensional (2D) and 3-dimensional (3D) imaging.

A continuing and unsolved problem with MR imaging is the presence of artifacts or "ghosts" caused by the motion of the human body. Body motion is generally described in two distinct ways: 1) as a periodic gross motion, which includes head and limb displacement, particularly where the motion is due to the more or less voluntary actions by the patient and cannot be determined a priori; and 2) physiological movement, which includes respiratory motion, cardiac pulsations, aortic pulsations, and gastrointestinal peristalsis, which is relatively periodic.

Ghosts are particularly apparent when the motion is periodic or nearly so, and is caused by the inconsistent appearance of the object from view to view. MR imaging techniques have evolved to such a point that the problems of motion artifacts are one of the few remaining limitations in MR technology. There currently exists no method to eliminate motion problems satisfactorily, particularly for generalized, a periodic motion. Accordingly, MR imaging is used extensively only in medical applications where the gross movement of the patient can be kept to a minimum. One example of such use is where a patient is given a brain scan. There, the patient is asked to keep his/her head still during data acquisition or the patient's head is immobilized using straps and other techniques which help minimize any motion of that part of the body being imaged. Where there is no motion, image artifacts do not present a problem. Thus, MR imaging is currently generally best used in obtaining images of the body where the patient's movement can be eliminated or restricted, thereby preventing or minimizing the appearance of ghosts and other motion artifacts which act to degrade the final image.

A particularly useful application of MR technology would be imaging of anatomical structures experiencing physiological motion, commonly manifested as periodic displacement due to respiration. Unfortunately, in this very important application of MR imaging, ghosting artifacts are especially problematic because, for example, typical abdominal images contain several moving anatomical structures, each generating ghosts with different shapes and positions. Such image artifacts make reading of the images difficult, and may possibly even lead to misdiagnosis.

In many imaging modalities, the measured signal $S(\vec{k})$ is collected in the spatial-frequency domain (known as k-space), resulting in the imaging equation $$S(\vec{k}) = \int_{-\infty}^{\infty} \rho(\vec{r}) e^{-2\pi i \vec{k}\cdot\vec{r}} d\vec{r},$$

where $\rho(\vec{r})$ is the desired image function. For stationary objects, k-space can be sufficiently sampled, and the image function $\rho(\vec{r})$ can be accurately recovered from the measured data by the discrete inverse Fourier transform. However, when the object is moving during data acquisition, as is the case with physiological motion, only a limited portion of k-space can be sampled instantaneously. If motion is ignored, as is often the case with conventional imaging methods, significant motion artifacts can arise. For example, for periodic or quasi-periodic motion, the motion effect manifests itself as image blurring and ghosting artifacts.

Over the past decade, several methods have been proposed to cope with motion artifacts. Such techniques have included, but have not been limited to, patient restraint, averaging, gating, ordered phase encoding, and various post-processing techniques. However, none of these attempts at reducing ghosting artifacts have fully succeeded.

Patient restraint, the simplest of all the solutions to implement is unfortunately also one of the least convenient for the patient. This method involves controlling the respiratory motion of patients by either asking them to hold their breaths, or by strapping the chest down to minimize the expansion of the chest or abdomen. It is obvious that such methods require absolute cooperation from the patient, which cooperation may not always be feasible or forthcoming. Additionally, even though chest motion may be preventable, other internal organs, such as the heart, obviously cannot be stilled.

Averaging, which is the process of averaging data acquired under conditions that are identical except for the motion, has the effect of attenuating the ghost artifacts and reducing random noise. In particular, the phase has the greatest significance for averaging. In fact, it is when the motion during each data set is offset in phase that the motion artifacts are attenuated. However, for averaging to be effective, a large number of data sets are required. In actual practice, up to eighteen data sets may be used in the averaging process. This results in a slowing down of the imaging process. Another disadvantage of this technique is that blurring caused by motion is not reduced.

Respiration normally imparts a spatial frequency dependence to the position of an anatomical structure. That is to say, respiration causes the subject to periodically vary in position. Respiratory gating is a method whereby image acquisition occurs only when the subject of the imaging has the same configuration as it had at a previous time. An inherent disadvantage of this method is that imaging times may take up to twice as long as normal.

Ordered phase encoding eliminates ghosts by acquiring data for periodic motion during one half or one period of the motion. This is accomplished by monitoring the motion, and from the displacement determining which views to acquire. Thus, after the views have been acquired, they are ordered so as to make motion appear monotonic. Although this method removes many of the ghosts without increasing the imaging time, it does not remove the blurring.

One of the most significant advances in motion compensation techniques is the use of navigator (NAV) echoes for estimating translational displacement parameters as described by R. L. Ehman and J. F. Felmlee in their article "Adaptive Technique for High-Definition MR Imaging of Moving Structures," *Radiology*, vol. 173, no. 1 pp. 255–63, October 1989. Generally, the NAV echo is similar to an image echo, except that no phase encoding or a small amount of constant phase encoding is applied thus its one-dimensional Fourier transform gives a projection throughout the navigator directions (NAV projections). NAV echoes are designed to permit tracking of the position of an object of interest within the field of view. Before or after each view, a NAV echo in either the frequency encoding or phase-encoding direction is acquired. A single NAV projection is then arbitrarily chosen as a reference, and cross-correlation functions are determined with respect to each of the other navigation projections. The peak location in the cross-correlation functions gives the relative displacement along the navigator direction. The disadvantage inherent in this technique is that only the in-plane bulk rigid-body motion along the navigator direction can be detected and subsequently removed. This is normally not the case in practical physiological motion, where the motion may be localized, non-rigid-body type and is arbitrary in direction.

Therefore, in spite of these advances in MR technology, imaging of time-varying objects remains a most challenging problem.

SUMMARY OF THE INVENTION

The invention relates most generally to magnetic resonance imaging. In accordance with one aspect of the invention, a (kt)-space model-based method is provided for imaging of time-varying objects with both high spatial and temporal resolution.

In accordance with another aspect of the invention, a generalized harmonic model is provided, which dictates both data acquisition and image reconstruction.

In accordance with still another aspect of the invention, several data acquisition schemes are provided which generate sufficient data for calculating the model parameters including motion frequencies and amplitudes.

A first advantage of the invention is its capability to generate snapshot images from time-varying objects with both high spatial and temporal resolution. This method recognizes the fact that the motion problem with imaging of dynamic objects is fundamentally an under-sampling problem along the time axis in (k,t)-space and overcomes it through the use of a novel generalized harmonic model.

Another advantage of the invention is to provide an effective method to remove image artifacts (ghosts and blurrings) from rigid-body or non-rigid-body, periodic or a periodic object motion.

Yet another advantage of the invention is that it does not require special imaging hardware and can be easily implemented in any commercial imaging system.

Still a further advantage of the invention is to create continuous MR images.

Further advantages of the invention will become apparent to those of ordinary skill in the art upon reading and understanding the following detailed description of the preferred embodiment.

DETAILED DESCRIPTION OF THE INVENTION

Figure 1:
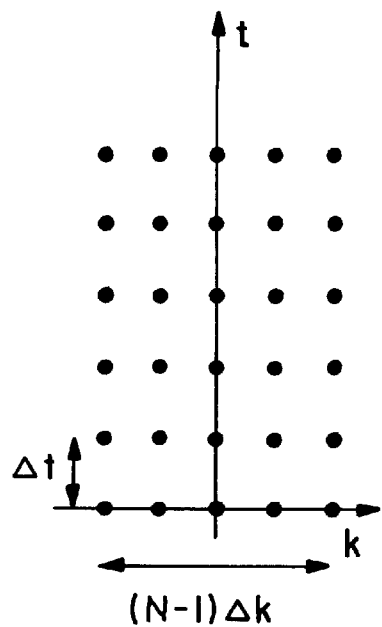
FIG. 1 depicts coverage of (k,t)-space with instantaneous sampling.
Figure 2:
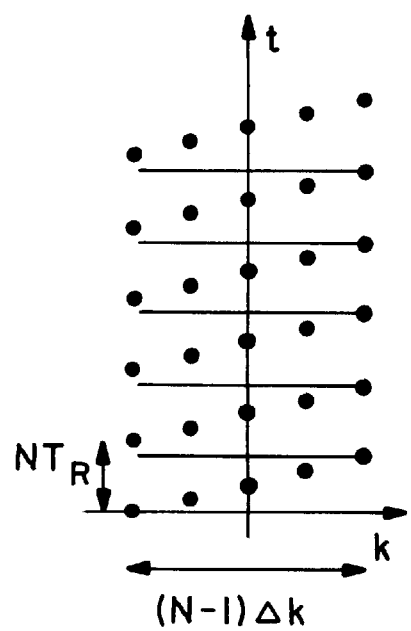
FIG. 2 depicts coverage of (k,t)-space with linear sampling.
Figure 3:
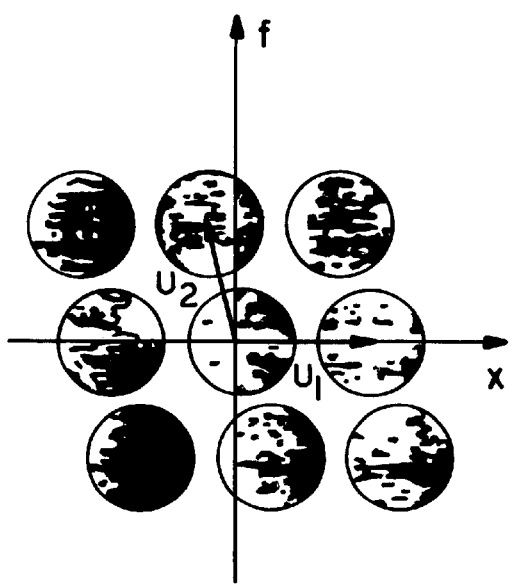
FIG. 3 depicts the resulting (x,f)-domain image from the image function of linear sampling in FIG. 2.

The (k,t)-space dynamic imaging technique described in the preferred embodiment can be understood by considering a one-dimensional (1D) dynamic imaging problem using phase encoding (assuming that data points in the readout direction can be collected instantaneously relative to the dynamic changes). After taking into account temporal variation, the image function becomes a 2D function, $\rho(x,t)$, of two independent variables: space (x) and time (t). If $\rho(x,t)$ is desired with temporal resolution $\Delta t$ and spatial resolution $1/N\Delta k$, an ideal snapshot technique would collect N instantaneous encodings during the time interval $\Delta t$, giving the (k,t)-space coverage in FIG. 1. In practice, a small but significant amount of time elapses between each encoding reading and therefore (k,t)-space is effectively sampled as shown in FIG. 2. Consequently, there is only one encoding available for each snapshot—the so-called time-sequential constraint. To reconstruct the spatiotemporal function $\rho(x,t)$ properly from this set of time-sequentially sampled data, the inventors treat it as a 2D problem, in contrast to the sequential 1D treatment in conventional techniques. Based on multi-dimensional sampling theory, the 2D Fourier transform of the sampled data is a periodic function, as depicted in FIG. 3 where the vertical axis represents the temporal-frequency distribution; the periodicity is defined by $$\vec{u}_1 = [1/(NT_R), 0]^t$$

and $$\vec{u}_2 = [-1/((N-1)\Delta k), 1/\Delta k]^t.$$

Exact reconstruction of $\rho(x,t)$ requires no overlapping between the periodic duplicates. Whether or not this condition is met largely depends on the temporal-frequency distribution of the dynamic changes. Assume that the maximum temporal-frequency of the dynamic changes is $f_{max}$ and the time interval between two successive encodings is $T_R$. The Nyquist requirement for an aliasing-free reconstruction is that $NT_R \leq 1/(2f_{max})$. In practice, this condition is rarely met, thus resulting in image errors often known as motion artifacts.

This problem can be overcome by use of an object model representing the dynamic image changes. Specifically, the temporal variations of each point are modeled by the generalized harmonic model $$\rho(\vec{r}, t) = \sum_{m=1}^{M(\vec{r})} c_m(\vec{r}) e^{i\omega_m(\vec{r})t}, \quad (2)$$

where M and $\omega_m$ are written as a function of $\vec{r}$ to signify the fact that motion frequency distribution is position-dependent. It is generally accepted that a harmonic model, with enough terms, can adequately represent spatial variation of an image function. Since temporal variation of an object is often simpler than its spatial variation, such a model is sufficient for modeling temporal variations. For example, if the intensity of an object is varying sinusoidally, the temporal variation can be represented by this model with a single frequency component. Generally, the model has many frequency components, but the amplitudes of higher-order terms decay rapidly. For rigid-body motion, these amplitudes decay asymptotically on the order of $1/\omega_m$. In many cases, the model can be simplified further by assuming that $\omega_m(\vec{r})$, $1 \leq m \leq M(\vec{r})$, are harmonically related. Consequently, model (2) can be rewritten as $$\rho(\vec{r}, t) = \sum_{m=1}^{M(\vec{r})} c_m(\vec{r}) e^{im\omega_0(\vec{r})t}, \quad (3)$$

where $\omega_o(\vec{r})$ is the fundamental frequency.

Without loss of generality, the $\vec{r}$-dependence of M and $\omega_m$ can be eliminated by rewriting Eq. (2) as $$\rho(\vec{r}, t) = \sum_{m=1}^{\hat{M}} c_m(\vec{r}) e^{i\omega_m t}, \quad (4)$$

where now $\hat{M}$ is the total number of motion frequency components for the entire object and $\omega_m$ accounts for all the possible motion frequencies present. With this model, the measured data are given by $$S(\vec{k}, t) = \int_{-\infty}^{\infty} \rho(\vec{r}, t) e^{-i2\pi \vec{k} \cdot \vec{r}} d\vec{r} \quad (5)$$

$$= \sum_{m=1}^{\hat{M}} \left[ \int_{-\infty}^{\infty} c_m(\vec{r}) e^{-i2\pi \vec{k} \cdot \vec{r}} d\vec{r} \right] e^{i\omega_m t}$$

$$= \sum_{m=1}^{\hat{M}} \alpha_m(\vec{k}) e^{i\omega_m t},$$

$$\text{where} \quad \alpha_m(\vec{k}) = \int_{-\infty}^{\infty} c_m(\vec{r}) e^{-2\pi \vec{k} \cdot \vec{r}} d\vec{r}. \quad (6)$$

Eq. (5) indicates that the measured data for each $\vec{k}$ value can also be described by a generalized harmonic model. By introducing the data model, the dynamic imaging problem can be converted to a parameter identification problem. In order to uniquely determine the model parameters, sufficient data have to be collected in (k,t)-space. Because of the inherent time-sequential constraint and the underlying under-sampling problem, data need to be acquired optimally to avoid image artifacts. An important property of this model is that if the motion frequencies are known a priori, the coefficients can be determined exactly in most cases even when (k,t)-space is under-sampled along the time axis.

Specifically, it has been determined that for a given $\vec{k}$ value, if L data points are taken at $t_1, t_2, \ldots t_L, \alpha_m(\vec{k})$ can be uniquely recovered from the measured data as long as $$(e^{i\omega_m t_1} e^{i\omega_m t_2} \ldots e^{i\omega_m t_L}) \neq (e^{i\omega_n t_1} e^{i\omega_n t_2} \ldots e^{i\omega_n t_L}), \text{ for } m \neq n. \quad (7)$$

If the temporal sampling is uniform such that $t_1 = l\Delta t$, the above condition can be re-stated as:

$$\omega_m \Delta t \neq \omega_n \Delta t \pm p 2\pi, \text{ for } m \neq n \text{ and any integer } p. \quad (8)$$

This property significantly relaxes the burden on data acquisition, and makes it possible to obtain high spatial and temporal resolution simultaneously. In practice, this model can be further simplified with a reduction in the number of model parameters by incorporating the harmonic constraints stated in Eq. (3). Thus, Eq. (5) becomes $$S(\vec{k}, t) = \sum_{p=1}^{P} \sum_{q=1}^{M_p} \alpha_{pq}(\vec{k}) e^{iq\omega_o(p)t}, \quad (9)$$

where P is the total number of fundamental motion frequencies, $\omega_o(p)$, each with $M_p$ harmonics.

Figure 4:
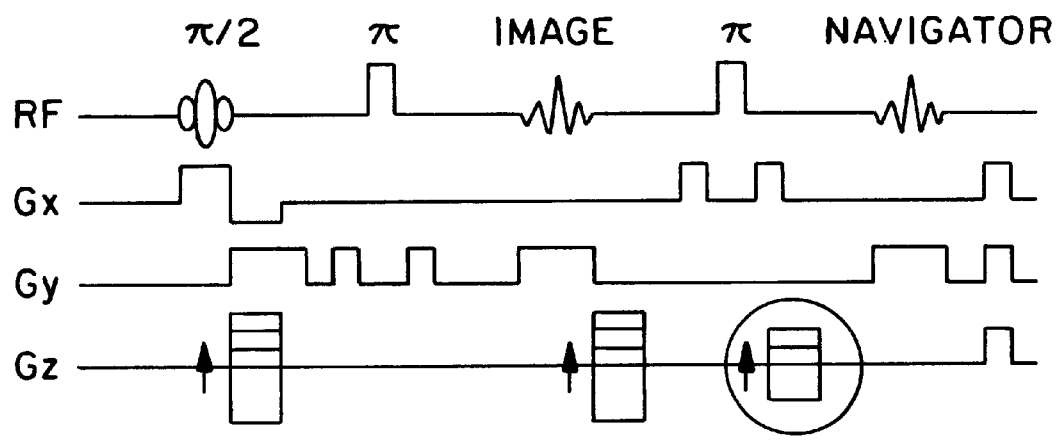
FIG. 4 depicts a two-dimensional spin-echo imaging pulse sequence with phase-encoded NAV echo.
Figure 5:
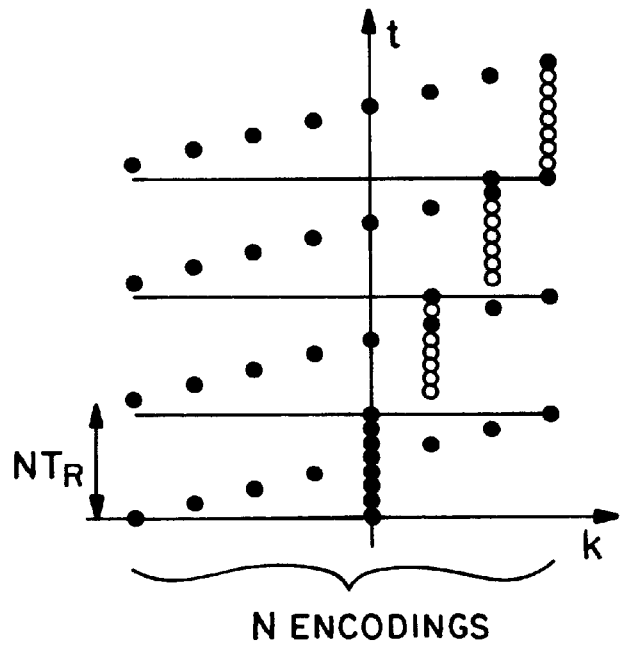
FIG. 5 illustrates coverage of (k,t)-space with dynamic imaging and phase-encoded NAV signals.
Figure 6:
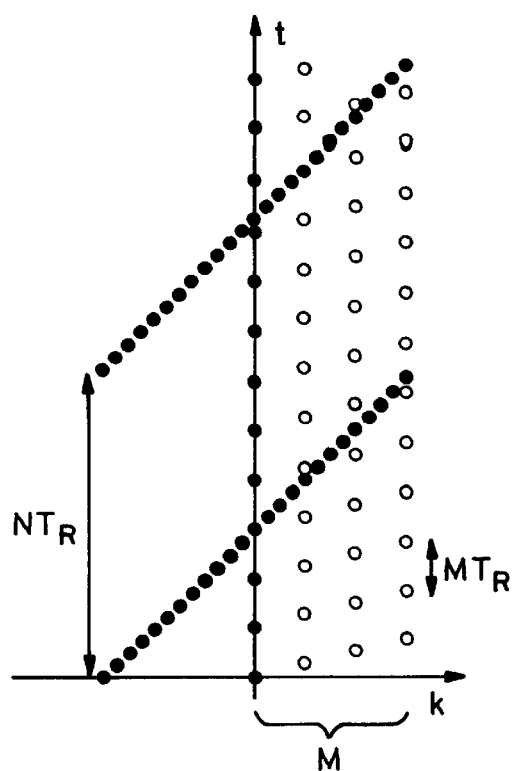
FIG. 6 depicts an alternate method of collecting NAV signals using one NAV echo per excitation distributed over M k-space lines.
Figure 7:
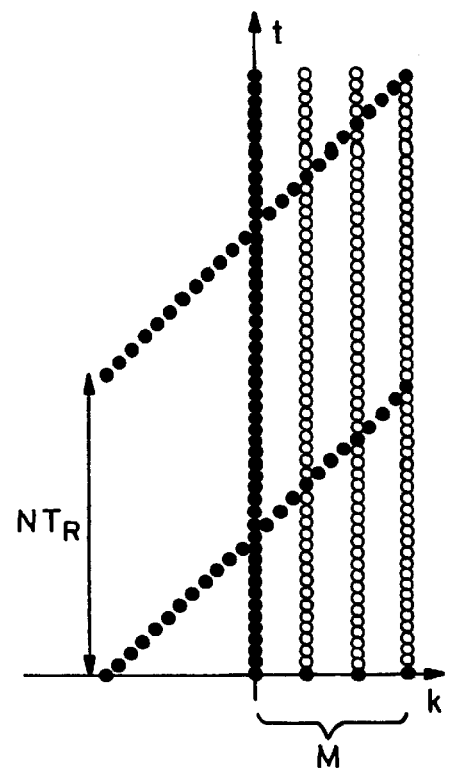
FIG. 7 depicts another alternative method of collecting NAV signals using the same (k,t)-space coverage as FIG. 6 but with M NAV echoes from each excitation.

Data acquisition of this invention is characterized by the collection of two separate data sets: one for determination of the motion frequencies and the other for determination of the amplitudes and subsequently used for formation of the dynamic images. While the amplitudes can be determined from aliased data, exact determination of the motion frequencies requires un-aliased data. There are many ways to provide this type of data in practice. For example, in cardiac imaging, ECG signals can be used to estimate the motion frequencies associated with cardiac motion. Additionally, EKG, EEG, or microradar signals commonly used for various types of motion detection may also be used. Finally, other sensing technologies such as optical and ultrasound can also provide data to be used in motion detection. For magnetic resonance imaging, a more direct approach is to collect these data while acquiring the dynamic imaging data. This can be accomplished using the well-known NAV echo excitation protocols. An example of such an excitation sequence is shown in FIG. 4, which generates one dynamic encoding and one or more reference encodings as the NAV signals. As can be seen from FIG. 5, the effective time sampling interval for the NAV signals is $\Delta t = T_R$ which should be small enough to satisfy the Nyquist sampling criterion. There is a variety of other ways to collect and distribute the NAV signals in (k,t)-space. Two such examples are shown in FIGS. 6, 7. In the first case, the NAV signals are properly encoded to cover M k-space lines. The advantage of this data collection scheme is improved motion sensitivity for the NAV signals since some types of motion may be transparent to some k-space data. The disadvantage is that the effective temporal sampling interval is now $MT_R$ which may violate the Nyquist sampling criterion if high motion frequency components are present. In that case, multiple NAV echo signals should be used as shown in FIG. 7.

Figure 8:
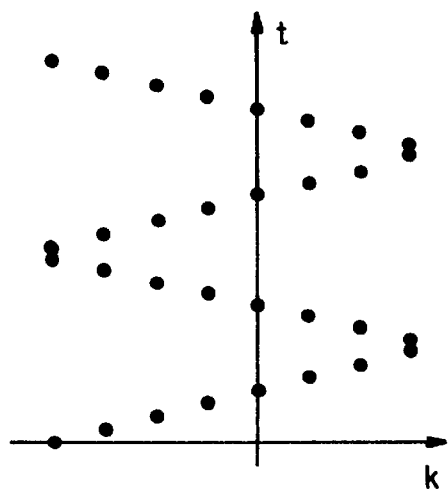
FIG. 8 illustrates an alternate method to cover (k,t)-space with dynamic imaging data using zig-zag sampling.
Figure 9:
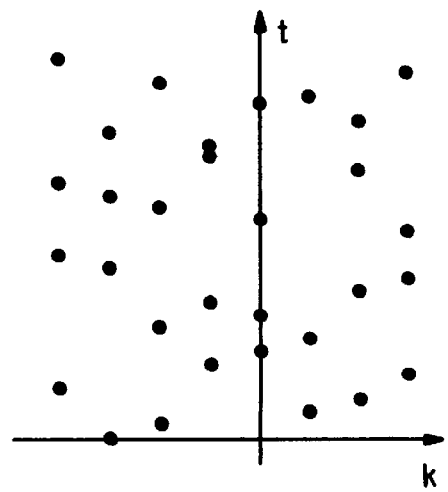
FIG. 9 illustrates a second alternate method to cover (k,t)-space with dynamic imaging data using random sampling.

Dynamic imaging data can be acquired in the conventional way, giving rise to the sampling pattern in FIG. 7. Other sampling patterns may also be used advantageously by properly ordering the phase-encoding steps. Two examples are shown in FIGS. 8, 9. In particular, the random sampling pattern in FIG. 9 may be desirable from the standpoint of satisfying the "unique reconstruction" condition of Eq. (7) or Eq. (8). In general, this method does not restrict how the dynamic encodings are applied as long as $\omega_m$ are known. But some sampling patterns may be better than others for determining the amplitudes of each motion frequency component based on a numerical stability consideration.

Figure 12:
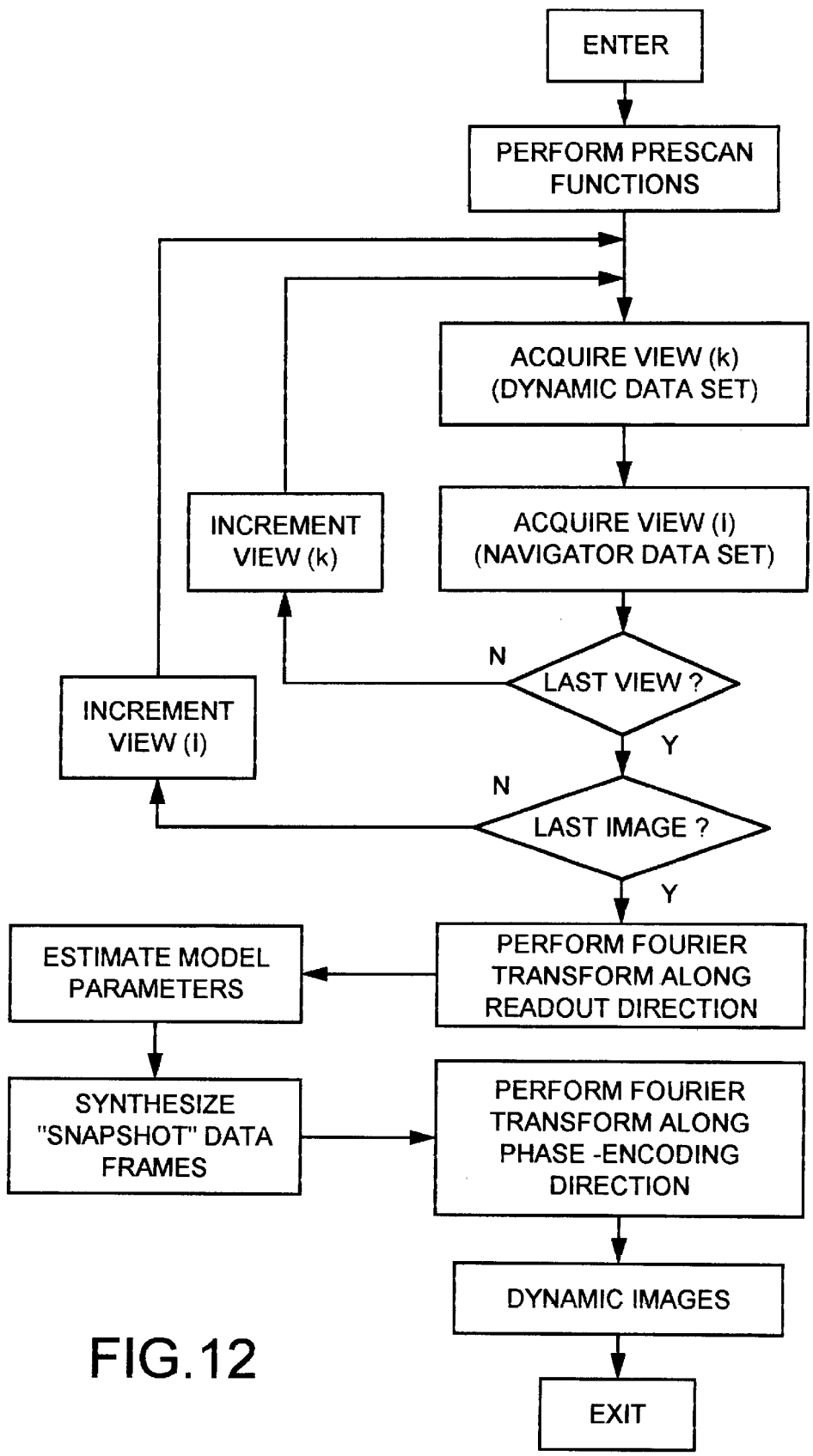
FIG. 12 is a block diagram of the data produced when practicing the preferred embodiment of the present invention.
Figure 13:
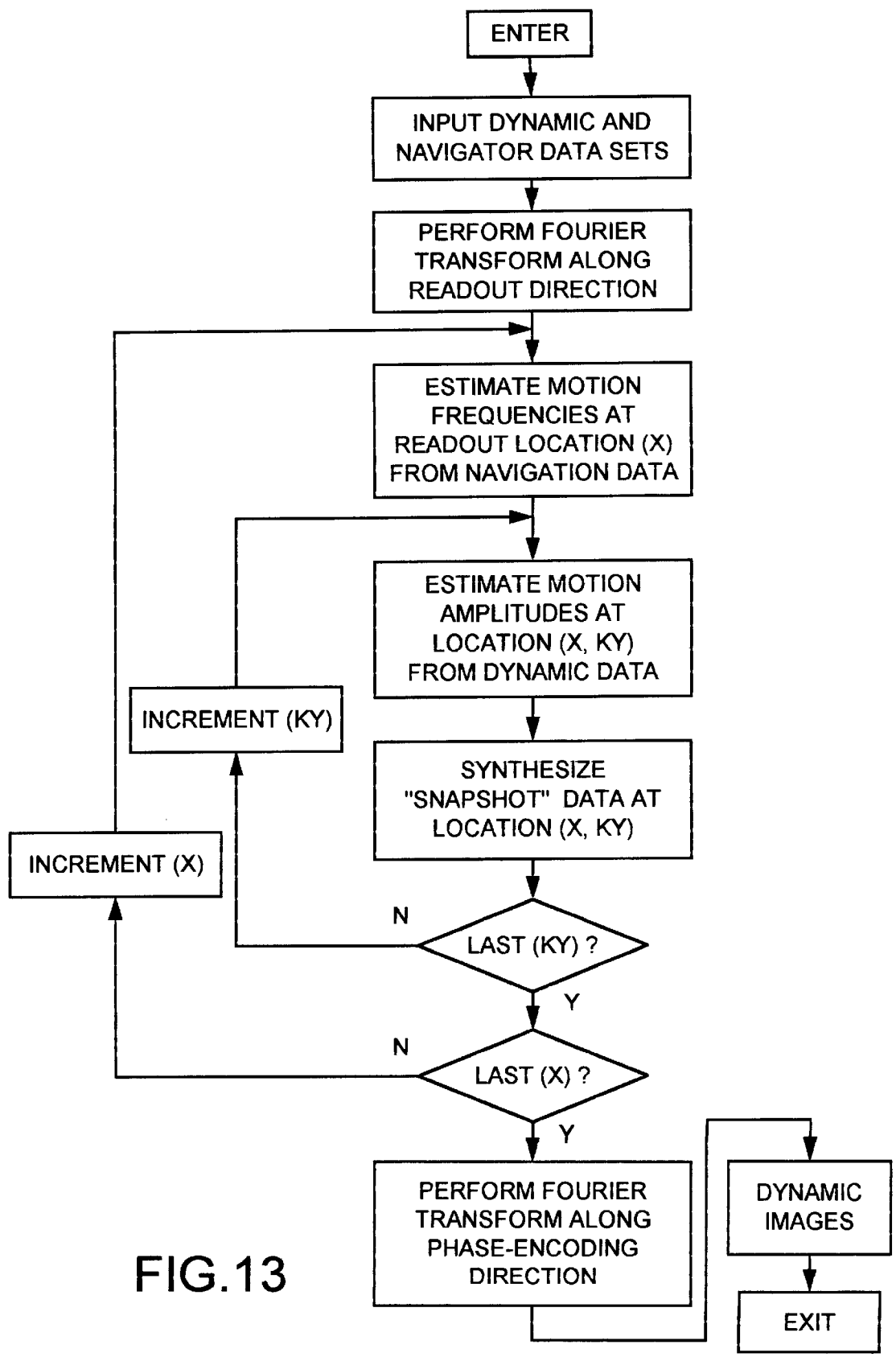
FIG. 13 is a flow chart of a program executed to carry out the preferred embodiment of the invention.

Referring to FIG. 12 and FIG. 13, with these data, reconstruction of the dynamic images consists of four major steps: (1) estimation of the motion frequencies from the NAV signals, (2) estimation of the amplitudes from the dynamic imaging data, and (3) data interpolation in (k,t)-space to generate "snapshot" data frames and (4) Fourier transform of each data frame to generate the snapshot images.

The first step is accomplished using block linear prediction (LP) or least squares fitting method. Specifically, assuming there are I sets of NAV signals each with length of L as $S^0_{ij}, 1 \leq i \leq I$ and $1 \leq j \leq L$, and the linear prediction order is p, then the following block linear prediction equation may be formed:

$$\begin{bmatrix} S^0_{1,1} & S^0_{1,2} & \cdots & S^0_{1,p} \\ S^0_{1,2} & S^0_{1,3} & \cdots & S^0_{1,p+1} \\ \vdots & \vdots & \ddots & \vdots \\ S^0_{1,L-p} & S^0_{1,L-p+1} & \cdots & S^0_{1,L-1} \\ S^0_{2,1} & S^0_{2,2} & \cdots & S^0_{2,p} \\ S^0_{2,2} & S^0_{2,3} & \cdots & S^0_{2,p+1} \\ \vdots & \vdots & \ddots & \vdots \\ S^0_{2,L-p} & S^0_{2,L-p+1} & \cdots & S^0_{2,L-1} \\ \vdots & \vdots & \ddots & \vdots \\ S^0_{I,1} & S^0_{I,2} & \cdots & S^0_{I,p} \\ S^0_{I,2} & S^0_{I,3} & \cdots & S^0_{I,p+1} \\ \vdots & \vdots & \ddots & \vdots \\ S^0_{I,L-p} & S^0_{I,L-p+1} & \cdots & S^0_{I,L-1} \end{bmatrix} \begin{bmatrix} \beta_1 \\ \beta_2 \\ \vdots \\ \beta_p \end{bmatrix} = - \begin{bmatrix} S^0_{1,p+1} \\ S^0_{1,p+2} \\ \vdots \\ S^0_{1,L} \\ S^0_{2,p+1} \\ S^0_{2,p+2} \\ \vdots \\ S^0_{2,L} \\ \vdots \\ S^0_{I,p+1} \\ S^0_{I,p+2} \\ \vdots \\ S^0_{I,L} \end{bmatrix} \quad (10)$$

The motion frequencies can be obtained from the LP coefficients $(\beta_1, \beta_2, \ldots \beta_p, 1)$ by taking the roots of the polynomial $$\beta_1 + \beta_2 Z + \beta_3 Z^2 + \ldots + \beta_p Z^{p-1} + Z^p = 0. \quad (11)$$

After the motion frequencies are known, the series coefficients are determined by the following linear system of equations, $$\begin{bmatrix} e^{i\omega_1 t_1} & e^{i\omega_2 t_1} & \cdots & e^{i\omega_{\hat{M}} t_1} \\ e^{i\omega_1 t_2} & e^{i\omega_2 t_2} & \cdots & e^{i\omega_{\hat{M}} t_2} \\ \vdots & \vdots & \ddots & \vdots \\ e^{i\omega_1 t_L} & e^{i\omega_2 t_L} & \cdots & e^{i\omega_{\hat{M}} t_L} \end{bmatrix} \begin{bmatrix} \alpha_1(\vec{k}) \\ \alpha_2(\vec{k}) \\ \vdots \\ \alpha_{\hat{M}}(\vec{k}) \end{bmatrix} = \begin{bmatrix} S(\vec{k}, t_1) \\ S(\vec{k}, t_2) \\ \vdots \\ S(\vec{k}, t_L) \end{bmatrix} \quad (12)$$

which can be solved using any of the existing linear system solvers. If L is larger than M (as is often the case), the system can be solved in a least squares sense. This system is always non-singular regardless of data under-sampling as long as the condition stated in Eq. (7) or Eq. (8) is met.

Figure 10:
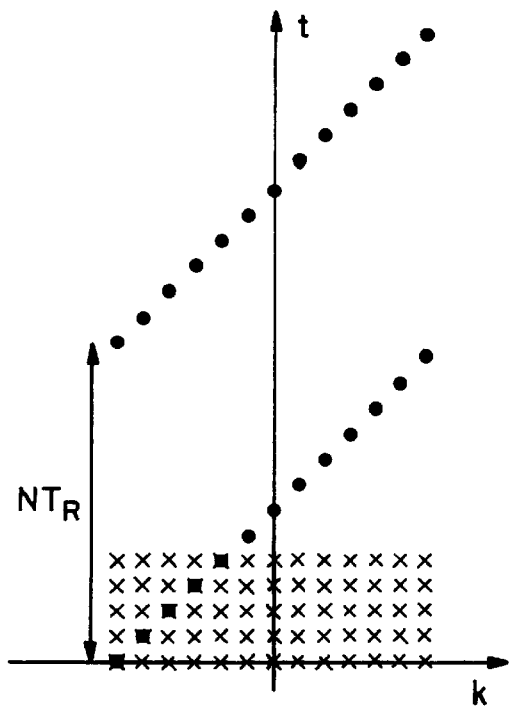
FIG. 10 shows sampling of (k,t)-space with measured (•) and synthetic (x) dynamic data from which each snapshot image is reconstructed.

After all the model parameters are known, a synthetic signal, $S(\vec{k},t)$, is generated from the model which is to be used to create instantaneous data frames as shown in FIG. 10. Finally each data frame is Fourier transformed to get the desired snapshot image at the temporal resolution $\Delta t = T_R$.

The invention may be implemented in conjunction with most well known MR imaging systems hardware. An example of one particular embodiment incorporating the present invention is applied in practice in the following manner in an MR system. A main computer system is provided having disk and tape storage capabilities for storing image data and the program of the present invention as shown in FIG. 12 and FIG. 13 which is responsible for acquiring the data sets used in motion parameter estimation and image reconstruction. The computer system also has an image processor for generating images from processed image data which have been collected, and an operator console which consists of a keyboard, a display terminal and a control panel. The computer system is further linked to a system controller which includes a microprocessor for initial processing of image data, a pulse generator, and a transceiver module. The system controller is itself controlled by the software contained in the main computer. The pulse generator produces data which determines the types of RF pulses which are to be produced and is interfaced to gradient amplifiers and a physiological acquisition controller. The gradient amplifiers indicate the type of pulses to be produced during the scan, and the physiological acquisition controllers are designed to receive signals such as EKG, ECG, EEG and other microradar signals from electrodes connected to the patient. These controllers provide the un-aliased data required to determine the motion frequencies. The system controller is then interfaced to a scan room assembly which connects to the actual MRI hardware which the patient is to be placed in. The hardware consists of a magnet assembly which includes gradient coils, the polarizing magnet, and an RF coil.

The pulse generator produces gradient waveforms which are applied to the gradient amplifiers, which in turn, excite the gradient coils in the magnet assembly. This process produces the magnetic field gradients which are used for position encoding the acquired signals, and is also used to generate the navigator signals. The transceiver, which is interfaced to the microprocessor, is also connected to the RF coil for sending and receiving radio waves and produces pulses which are amplified by an RF amplifier. The signals which are generated by the excited nuclei (NMR signals) in the patient, are sensed by the RF coil and further amplified and digitized by the transceiver. This digitized data is then transferred to the system controller for initial image processing which processes the data according to the method described above and as shown in FIG. 12 and FIG. 13, thereby resulting in motion artifact free snapshots of the patient. These snapshot images may then be stored on the main computer, and may also be used for further image processing such as creating a "motion picture" image of the patient.

Figure 11:
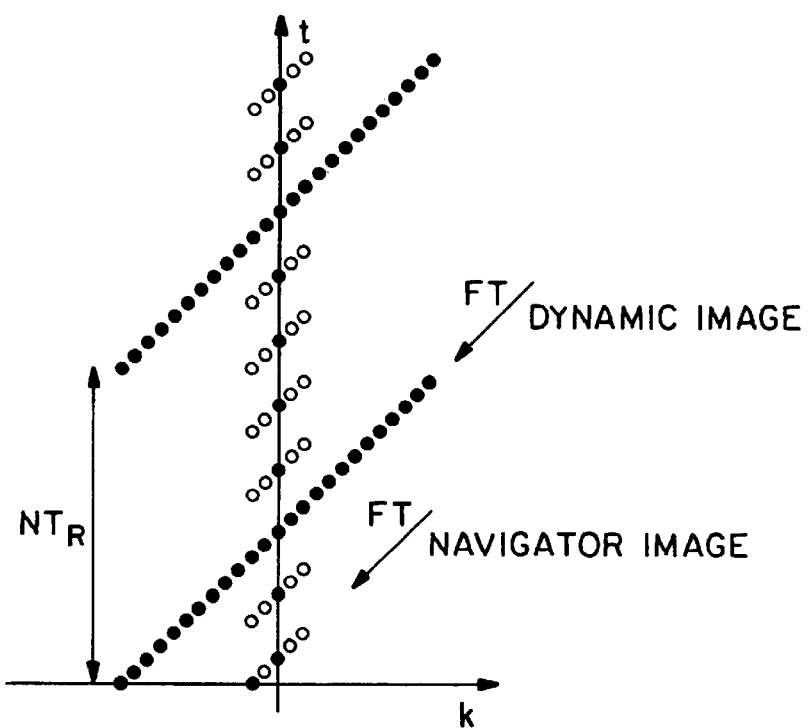
FIG. 11 shows sampling of (k,t)-space with high-spatial-resolution dynamic data (•) and low-spatial-resolution NAV data (○).

The present invention has been described with respect to certain embodiments and conditions which are not meant to and should not be construed to limit the scope of the invention. Many variants of this scheme will become obvious to those skilled in the art after reading this disclosure. For example, instead of identifying all the model parameters in (k,t)-space, it is sometimes more advantageous to perform model fitting in (r,t)-space by first Fourier transforming each dynamic imaging data frame and NAV data frame as shown in FIG. 11. It is easy to prove, based on the projection-slice theorem, that the resulting images are projection images of $\rho(\vec{r},\omega)$ with appropriate linear phase shift along the ω axis. Or in other words, motion information is phase-encoded in the resulting (r,t)-space images thus obtained. Consequently, the low resolution NAV images can be fitted with the generalized harmonic image model to provide localized motion frequencies. After that, the amplitude parameters can be determined from the dynamic images by least squares fitting. A distinct advantage of performing (r,t)-space fitting over (k,t)-space fitting is that motion information is spatially localized. This leads to a reduction of model order and improved parameter estimation.

What is claimed is:

1. A method for obtaining high-resolution images of a moving object, the method comprising the steps of:
   acquiring a set of navigator signals from the moving object according to a generalized harmonic model of object motion for the moving object;
   acquiring a sequence of dynamic data frames from the moving object according to the generalized harmonic model of the object motion; and
   reconstructing a sequence of high-resolution dynamic images using the set of navigator signals and the sequence of dynamic data frames according to the generalized harmonic model of the object motion.

2. The method according to claim 1 wherein the navigator signals include at least one of (a) phase-encoded magnetic resonance navigator echos, (b) frequency-encoded magnetic resonance navigator echoes, (c) electrical EKG signals, (d) sonic signals, (e) ultrasonic signals, (f) pressure signals, (g) high temporal signals and (h) microradar signals.

3. The method according to claim 2 including the step of utilizing the navigator signals to cover (k,t)-space so that the temporal changes of the moving object can be determined for the generalized harmonic model.

4. The method according to claim 1 wherein the dynamic frames are acquired through magnetic resonance phase-encoding having a number of encodings per data frame determined by a desired spatial resolution of the high-resolution dynamic images.

5. The method according to claim 1 wherein the dynamic data frames are acquired through magnetic resonance frequency-encoding having a number of encodings per data frame determined by a desired spatial resolution of the high-resolution dynamic images.

6. The method according to claim 5 including the step of employing the dynamic data frames to cover (k,t)-space in a linear sequential order according to the generalized harmonic model of the object motion.

7. The method according to claim 1 wherein the generalized harmonic model in $(r,t)$-space is defined by: $\rho(\vec{r},t) = \sum_{m=1}^{\vec{M}(\vec{r})} c_m(\vec{r}) e^{i\omega_m(\vec{r})t}$ and $(k,t)$-space is defined by: $S(\vec{k},t) = \sum_{m=1}^{\vec{M}} \alpha_m(\vec{k}) e^{i\omega_m t}$ where $\rho(\vec{r},t)$ and $S(\vec{k},t)$ are spatio-temporal image functions of the moving object, $c_m(r)$ and $\alpha_m(k)$ are amplitude parameters of the moving object, $\omega_m$ is a motion frequency parameter of the object, $e^{i\omega_m(r)t}$ and $e^{i\omega_m t}$ are functions of the motion frequency of the object, m is a motion frequency component of the object and $\vec{M}$ is the total number of motion frequency components.

8. A method for obtaining high-resolution images of a moving object, the method comprising the steps of:
   acquiring a set of navigator signals from the moving object;
   acquiring a sequence of dynamic data frames from the moving object;
   estimating motion frequency parameters of the object from the navigator signals;
   estimating amplitude parameters of the data frames in (k,t)-space;
   using a generalized harmonic model to recover missing data in (k,t)-space to provide snapshot data frames; and
   Fourier transforming the snapshot data frames to generate snapshot images of the object.

9. The method according to claim 8 wherein the step of estimating motion frequency parameters comprises the step of fitting the generalized harmonic model to the navigator signals in a least-squares sense.

10. The method according to claim 9 wherein the fitting step comprises the step of using a block linear prediction algorithm.

11. The method according to claim 9 wherein the fitting step comprises the step of using a numerical algorithm.

12. The method according to claim 8 wherein the step of estimating amplitude parameters comprises the step of fitting the generalized harmonic model to the dynamic data frames in a least-squares sense.

* * * * *